(12) United States Patent
Nihei et al.

(10) Patent No.: US 8,859,279 B2
(45) Date of Patent: Oct. 14, 2014

(54) CELL DETACHMENT METHOD

(75) Inventors: Amiko Nihei, Chiba (JP); Masatsugu Shigeno, Chiba (JP); Yoshiharu Shirakawabe, Chiba (JP); Akira Inoue, Chiba (JP); Osamu Matsuzawa, Chiba (JP); Naoya Watanabe, Chiba (JP)

(73) Assignee: Hitachi High-Tech Science Corporation (JP)

( * ) Notice: Subject to any disclaimer, the term of this patent is extended or adjusted under 35 U.S.C. 154(b) by 1890 days.

(21) Appl. No.: 11/810,768

(22) Filed: Jun. 7, 2007

(65) Prior Publication Data

US 2007/0292946 A1 Dec. 20, 2007

(30) Foreign Application Priority Data

Jun. 20, 2006 (JP) .................................. 2006-169822

(51) Int. Cl.
*C12N 5/00* (2006.01)
*C12M 1/00* (2006.01)

(52) U.S. Cl.
CPC .................................... *C12M 47/04* (2013.01)
USPC .......................................... 435/325; 850/62

(58) Field of Classification Search
None
See application file for complete search history.

(56) References Cited

FOREIGN PATENT DOCUMENTS

| JP | 2005160370 | 6/2005 |
|----|------------|--------|
| WO | 0210349 | 2/2002 |

OTHER PUBLICATIONS

Boyd et al., "Use of the Atomic Force Microscope to Determine the Effect of Substratum Surface Topography on Bacterial Adhesion", Langmuir, 2002, vol. 18, pp. 2343-2346.*
Fukada et al., "Micropatterned cell co-cultures using layer-by-layer deposition of extracellular matrix components", Biomaterials, available online Oct. 19, 2005, vol. 27, pp. 1479-1486.*
Wadu-Mesthrige et al., "Fabrication of Nanometer-Sized Protein Patterns Using Atomic Force Microscopy and Selective Immobilization", Biophysical Journal, Apr. 2001, vol. 80, pp. 1891-1899.*
Sagvolden et al. "Cell Adhesion Force Microscope", Proc Natl Acad Sci , Jan. 1999, vol. 96, pp. 471-476.*
Puech et al., "Measuring cell adhesion forces of primary gastrulating cells from zebrafish using atomic force microscopy", Journal of Cell Sciences, 2005, vol. 118, pp. 4199-4206.*
Simon et al., "Characterization of Dynamic Cellular Adhesion of Osteoblasts Using Atomic Force Microscopy", Cytometry Part A, 2003, vol. 54A, pp. 36-47.*

* cited by examiner

*Primary Examiner* — Laura Schuberg
(74) *Attorney, Agent, or Firm* — Adams & Wilks

(57) ABSTRACT

A cell detachment method for detaching only a desired cell from a plurality of cells cultured on a substrate under predetermined culture environment conditions by using a scanning probe microscope having a probe, comprising: observing the plural cells; specifying the cell to be detached; moving the probe onto the specified cell; and pressing the prove against the specified cell with a predetermined force so as to detach the cell from the substrate.

17 Claims, 8 Drawing Sheets

XY DIRECTIONS

Z DIRECTION

CELL DETACHMENT METHOD

This application claims priority to Japanese Patent Application No. 2006-169822 filed Jun. 20, 2006, the entire content of which is hereby incorporated by reference.

BACKGROUND OF THE INVENTION

This invention relates to a cell detachment method for detaching a cell during a culture (cultured cell) from a substrate.

In the case of culturing cells, two methods are mainly employed in general. Namely, the two methods are a method of culturing cells in a state where the cells are allowed to float in a culture solution and a method of culturing cells in a state where the cells are spread on a purpose-built substrate (cell). Of the two methods, the culture method using substrate is employed more frequently since it has advantages such as easy observation using a microscope and capability of culturing plural cells as one lot as compared to the culture in which the cells are allowed to float. More specifically, since the cells are spread on the substrate in the culture method using substrate, the cells are immobile and stable, thereby making it possible to easily observe a culture process with a microscope. Also, since it is possible to culture the plural cells in a state where they are attached to one another to perform intercellular signaling, it is possible to conduct culturing in a state which is similar to the natural state. Therefore, the culture method using substrate is widely used at present.

Referring to FIG. 10, in the case of conducting a culture by employing the culture method using substrate, each of cells S adheres to a substrate 30 and adjacent cells S. Such adhesion is caused because the cell S secretes an extracellular matrix S', i.e. a protein substance which is an adhesive substance, on its surface upon contact with the substrate 30 or the adjacent cells S and because an adhesive force of the cell itself is increased inside the cell. As a result, the plural cells S adhere to the substrate 30 in a state where they are attached to one another as shown in FIG. 10. The cells S gradually proliferate while maintaining the above-described state to increase in number.

When the cells S have proliferated to achieve the required number of cells, the cells are no longer cultured on the substrate 30 and are generally detached at least once from the substrate 30 to be transferred onto a larger substrate to be cultured thereon. Also, in the case of taking out the cells S that have proliferated to achieve a certain number of cells, it is necessary to detach the cells from the substrate 30.

In order to perform the detachment of the cells, various methods have been employed. For example, there has been known a method of physically scraping off cells S that adhere to a substrate 30 by using a cell scraper 31 as shown in FIG. 11. Also, as shown in FIG. 12, there has been known a method of detaching cells S by separating the cells from one another by a chemical treatment using a reagent T and including a collagenase treatment and a trypsin treatment (see Patent Publication 1, for example).

Also, as shown in FIG. 13, there has been known a method of detaching cells S by using a cell culture sheet 32 provided on a substrate 30 (see Patent Publication 2, for example).

The cell culture sheet 32 is a stimulus-responsive substrate of which characteristics are switched between a state wherein the cells S adhere easily thereto and a state wherein the cells S hardly adhere thereto upon reception of stimulation such as a temperature, pH, and light. For example, during a culture of the cells S, the cell culture sheet 32 is brought into a state wherein the cells S adhere easily thereto. Then, the state is changed into the state wherein the cells S hardly adhere thereto by changing a temperature for detaching the cells S. Thus, it is possible to detach the entire cells from the cell culture sheet 32 due to the reduction in adhesiveness. Particularly, since this method enables to detach the entire culls, it is suitably used for a horny coat culture, a skin culture, and the like.

[Patent Publication 1] JP-A-2005-160370
[Patent Publication 2] International Publication No. 02/10349

However, the following problems are left unsolved in the conventional methods.

With the method of physically detaching cells using the scraper 31, a death rate of the cells S is high since the cells S are damaged by the scraper 31, and it is difficult to conduct a passage culture. The same problem has been found in the case of conducting the detachment by performing the chemical treatment using the reagent T.

Further, since the entire cells adhered to the substrate 30 are detached at once with the methods, the methods do not enable to detach only a desired cell S or desired cell group from the cells S and are difficult to operate.

The method using the cell culture sheet 32 enables the detachment with a reduced damage as compared to the physical detachment method and the detachment method by way of chemical treatment. That is, since the method enables the detachment with a temperature change which prevents the cells S from being damaged (the cells S are destroyed or a proliferation speed is remarkably reduced when the temperature change is out of lower limit critical solution temperatures of 0 to 80° C.), it is possible to reduce the damage of the cells S.

However, since the entire cells are detached by this method, the method does not enable to detach only a desired cell S or desired cell group from the cells S and is difficult to operate as is the case with the above-described methods.

Also, since the culture is conducted on a special culture substrate in which the cell culture sheet (ex. a temperature responsive polymer) 32 is provided on the substrate 30, such culture environment can be unsuitable for a certain type of cells S.

This invention has been accomplished in view of the above-described circumstances, and an object thereof is to provide a cell detachment method for detaching only a desired cell or cell group from plural cells cultured on a substrate without influencing on other cells.

SUMMARY OF THE INVENTION

In order to attain the above object, this invention provides the following measures.

A cell detachment method according to this invention is a method for detaching only a desired cell from a plurality of cells cultured on a substrate under predetermined culture environment conditions by using a scanning probe microscope having a probe and characterized by comprising: an observation step for observing the plural cells and specifying the cell to be detached; a moving step for moving the probe onto the specified cell, the moving step being performed after the observation step; and a stimulation step for giving physical stimulation to the specified cell by pressing the probe against the specified cell with a predetermined force in order to detach the cell from the substrate, the stimulation step being performed after the moving step.

In the cell detachment method according to this invention, the plural cells are initially cultured as being spread on the substrate such as a purpose-built cell that is kept under the predetermined culture environment conditions (ex. in a culture medium of about 37° C. and a constant carbon dioxide concentration). In this state, each of the cells adheres to the substrate and the adjacent cells via a secreted extracellular matrix.

The observation step is performed during the culture. More specifically, the plural cells are observed by using an observation unit such as an optical microscope, and, when the cell to be removed is found as a result of the observation, a position of the cell is specified. For example, a mutant cell, a cell with a certain abnormality, or the like is specified.

Next, the moving step for moving the probe onto the specified cell by appropriately operating the scanning probe microscope is performed. In this step, it is possible to correctly position the probe onto the specified cell by using the observation unit used in the observation step.

Next, the scanning probe microscope is appropriately operated again to perform the stimulation step for giving physical stimulation to the specified cell by pressing the probe against the specified cell with the predetermined force for a certain period of time. Upon reception of the stimulation, activity of the cell is temporarily stopped, and an adhesive force is weakened. Accordingly, the cell can no longer adhere to the substrate and the adjacent cells and starts to float in the culture medium W. As a result, it is possible to remove the cell specified in the observation step by detaching the cell from the substrate.

Particularly, since only the specified cell is detached from the substrate by giving the stimulation only to the specified cell, no influence is exerted on the rest of the cells, and the rest of the cells continue to adhere. In other words, as is different from the conventional detachment methods in which the cells are subject to damage and the entire cells are inevitably detached at once, it is possible to detach only the desired cell from the plural cells cultured on the substrate without influencing on the rest of the cells. Therefore, it is possible to perform the detachment that has been too difficult to perform with the conventional methods, thereby making it possible to perform various cultures. Also, since it is possible to continue the culture of the rest of the cells by using the same substrate, this method provides the handling easiness.

Further, since the special substance such as the conventional cell culture sheet is not used in this invention, this invention is free from restriction by the type of cells. Also, since the stimulation given to the cell to be detached is not more than the predetermined force that temporarily stops the activity of the cell, it is possible to suppress as much as possible the influence to be exerted on the cell, and crushing or the like of the cell does not happen. From this standpoint, too, this invention does not exert any influences on the rest of the cells and the culture environment.

The cell detachment method of this invention according to the above-described cell detachment method of this invention is characterized in that the force for pressing the probe is decided depending on at least one of conditions of a type of the specified cell, a size of the specified cell, and a culture state.

In the cell detachment method according to this invention, the force for pressing the probe onto the cell is suitably changed depending on at least one of conditions of a type of the specified cell, a size of the specified cell, and a culture state. Accordingly, it is possible to give the stimulation to the cell to be detached while minimizing influence to be exerted on the cell. Preferably, the force for pressing the probe is less than 100 μN.

Also, the cell detachment method of this invention according to the above-described cell detachment method of this invention is characterized in that the observation step, the moving step, and the stimulation step are repeated during a culture of the rest of the cells after detaching the specified cell.

In the cell detachment method according to this invention, the observation step is performed during the culture of the rest of the cells after detaching the specified cell when so required. As a result, in the case where a cell (cell mutant or the like) that is unnecessary for the culture appears again in the course of progress of the culture, the moving step and the stimulation step are performed again to remove the cell. Accordingly, it is possible to culture only the necessary cells in the case of performing a long term culture.

Also, the cell detachment method of this invention according to any one of the above-described cell detachment methods of this invention is characterized in that the stimulation is given to the specified cell while scanning a surface of the cell in the state where the probe is pressed against the cell when performing the stimulation step.

In the cell detachment method according to this invention, when performing the stimulation step, the probe is not only pressed against the cell but also the surface of the cell is scanned while pressing the probe against the cell. Accordingly, since it is possible to give the stronger stimulation, it is possible to reliably detach the cell even when the cell adheres firmly. Particularly, in the case where the size of the cell is large, it is possible to detach the cell more easily since it is possible to give the stimulation uniformly to a whole part of the cell.

Also, the cell detachment method of this invention according to any one of the above-described cell detachment methods of this invention is characterized in that the stimulation is given to the specified cell with the probe being vibrated in at least one of a direction vertical to a surface of the substrate and a direction horizontal to the surface of the substrate in the state where the probe is pressed against the cell when performing the stimulation step.

In the cell detachment method according to this invention, the probe is not only pressed against the cell but also vibrated at least one of XY-directions (directions horizontal to the surface of the substrate) and a Z-direction (direction vertical to the surface of the substrate) while being pressed against the cell in the stimulation step. In other words, the probe is pressed while being vertically vibrated in the Z-direction, while being horizontally vibrated in the XY-directions, or while being vertically and horizontally vibrated in the Z-direction and the XY-directions. Accordingly, since it is possible to give the stronger stimulation to the cell, it is possible to detach the cell even when the cell adheres firmly.

Also, the cell detachment method of this invention according to any one of the above-described cell detachment methods of this invention is characterized by comprising a co-culture step for co-culturing a cell of a different type by placing the different cell at a position of the detached cell, the co-culture step being performed after the stimulation step.

In the cell detachment method according to this invention, the different cell is placed at a vacant position on the substrate, i.e. the position where the detached cell adhered, after detaching the cell in the stimulation step. The different cell adheres to the substrate by secreting an extracellular matrix in the course of time. Therefore, it is possible to co-culture at least two types of cells.

Also, the cell detachment method of this invention according to any one of the above-described cell detachment methods of this invention is characterized by comprising a capturing step for capturing the detached cell, the capturing step being performed after the stimulation step.

In the cell detachment method according to this invention, the capturing step for capturing (pinching) by using a pipette or the like the cell floating in the culture medium is performed after the cell detachment by the stimulation step. Accordingly, since it is possible to eliminate the cell from the culture environment, it is possible to further reduce the influence to be exerted on the rest of the cells.

Also, the cell detachment method of this invention according to the above-described cell detachment method of this invention is characterized by comprising a passage culture step for culturing the captured cell on another substrate under predetermined culture environment conditions, the passage culture step being performed after the capturing step.

In the cell detachment method according to this invention, it is possible not only to eliminate the cell captured in the capturing step but also to perform the culture by placing the cell on the different substrate kept under the predetermined culture environment conditions by performing the passage culture step. This method is effective for the case of detaching normal cells for the purpose of thinning and the like. Accordingly, it is possible to effectively use the cells without wasting the cells.

With the cell detachment method according to this invention, it is possible to detach only a desired cell from a plurality of cells cultured on a substrate without influencing on the rest of the cells.

BRIEF DESCRIPTION OF THE DRAWINGS

FIGS. 9A to 9D are diagrams for explaining Example performed for actually detaching a cell by employing the cell detachment method according to this invention, wherein: FIG. 9A shows a diagram showing four cells before the detachment; FIG. 9B shows a state immediately after the detachment of one of the cells from the state of FIG. 9A; FIG. 9C shows a state of the rest of the cells 10 minutes after the detachment; and FIG. 9D shows a state of the rest of the cells 30 minutes after the detachment.

DETAILED DESCRIPTION OF THE INVENTION

Figure 1:
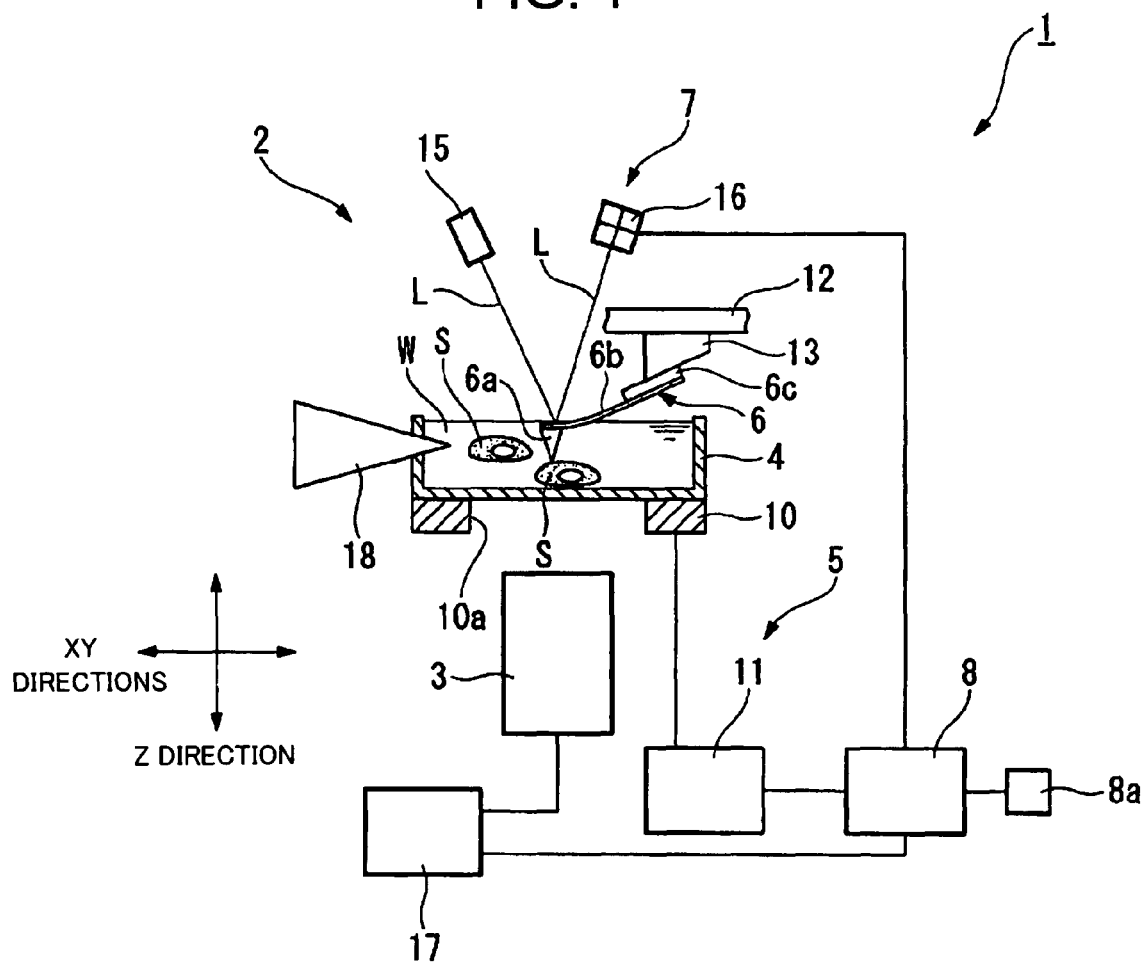
FIG. 1 is a block diagram showing one embodiment of a cell detachment system to be used for performing a cell detachment method according to this invention.

Hereinafter, one embodiment of the cell detachment method according to this invention will be described with reference to FIGS. 1 to 5. In this embodiment, a case of performing cell detachment by using a cell detachment system 1 wherein a scanning probe microscope 2 and an optical microscope 3 are combined as shown in FIG. 1 will be described by way of example.

The scanning probe microscope 2 is provided with a moving unit 5 for moving in three-dimensional directions a cell (substrate) 4 for culturing a plurality of cells S, a probe unit 6 having a probe 6a at the tip of a lever 6b, a displacement measurement unit 7 for measuring a deflection of the lever 6b, and a control unit 8 such as a personal computer for controlling these component parts in an integrated manner.

The cell 4 which is retained on an XYZ scanner 10 is formed from an optically transparent material and has a sectional shape of a substantially U-shape of which an upper part is opened. A culture medium (a culture solution containing components required by the cells for functioning normally) W is stored inside the cell 4, and the plural cells S are cultured as being spread at the bottom of the cell 4. Also, a heater (not shown), a carbon dioxide supply unit (not shown), and the like are incorporated into the cell 4 so that the cells S are cultured under predetermined conditions. For example, the culture medium W is adjusted in such a manner that a temperature and a carbon dioxide concentration of the culture medium W are 37±0.5° C. and 5%. Further, the culture medium W is circulated via a piping (not shown) so that a fresh culture medium W is continuously supplied.

The XYZ scanner 10 is a piezoelectric element formed of PZT (lead zirconate titanate) and the like, for example, and moves minutely in three directions of XY-directions (directions horizontal to the bottom of the cell 4) and a Z-direction (direction vertical to the bottom of the cell 4) when a voltage is applied from a drive circuit 11 in response to an amount and a polarity of the applied voltage. Accordingly, it is possible to move the cell 4 in the XY-directions and the Z-direction. In other words, the XYZ scanner 10 and the drive circuit 11 form the moving unit 5.

Figure 2:
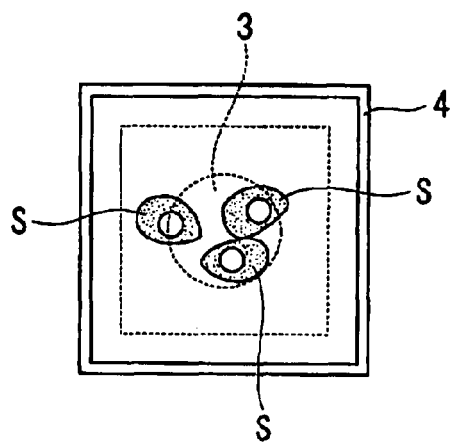
FIG. 2 is a diagram showing a cell of the cell detachment system of FIG. 1 as viewed from above.

Since the XYZ scanner 10 has a cylindrical shape that has an opening 10a having a square sectional shape in its center as shown in FIG. 2, it does not intersect a light path of the optical microscope 3 described later.

The lever 6b has its rear end supported by a main body 6c in a cantilever fashion. In other words, the probe unit 6 is formed of the probe 6a, the lever 6b, and the main body 6c. Also, the probe unit 6 is attachably/detachably fixed to a slope block 13 via the main body 6c by a wire or the like, and the slope block 13 is fixed to a lower surface of a holder main body 12. The probe unit 6 is fixed in such a fashion that the lever 6b is inclined by the slope block 13 by a predetermined angle with respect to the bottom of the cell 4. Also, a position of the probe unit 6 is adjusted by the holder main body 12 so that at least the probe 6a is soaked in the culture medium W.

A semiconductor laser light source 15 for emitting laser light L and a laser light receiving unit 16 for receiving the laser light L reflected by the reflection surface of the lever 6b are attached to a mounting (not shown) disposed above the probe unit 6. The laser light receiving unit 16 is a tetrameric photo-detector, for example, and detects a change in deflection of the lever 6b based on a position of incidence of the laser light L. The laser light receiving unit 16 converts the detected deflection change of the lever 6b into a deflection signal to output the signal to the control unit 8. That is, the semiconductor laser light source 15 and the laser light receiving unit 16 form the displacement measurement unit 7.

The control unit 8 stops the drive circuit 11 when the deflection signal sent from the laser light receiving unit 16 reaches to a preliminary set rated value. With such constitution, it is possible to press the probe 6a against the cell S with a predetermined force. In this embodiment, the rated value is set in accordance with the type of the cell S.

Also, an operation unit 8a to be used by an operator for inputting various conditions and operating the drive circuit 11 and the like is connected to the control unit 8. With such constitution, the operator can move the XYZ scanner 10 appropriately in the three-dimensional directions via the operation unit 8a.

The optical microscope 3 is disposed below the XYZ scanner 10 so as to enable observation of a culture state of the plural cells S from a direction of a lower surface of the cell 4 through the opening 10a of the XYZ scanner 10. Also, the optical microscope 3 outputs the observed image to a monitor 17 connected to the control unit 8. With such constitution, the operator can specify a position of the cell S by using the operation unit 8a while monitoring the image displayed on the monitor 17.

Hereinafter, a description will be given on a cell detachment method for detaching only the desired cell from the plural cells S cultured in the cell 4 by using the cell detachment system 1 having the above-described structure.

In the cell detachment method of this embodiment, an observation step for observing the plural cells S and specifying the cell S to be detached from the observation result; a moving step for moving the probe 6a onto the specified cell S after the observation step; a stimulation step for giving physical stimulation to the specified cell S by pressing the probe 6a against the cell S with a predetermined force to detach the cell S from the bottom of the cell (substrate) 4 after the moving step; and a capturing step for capturing the detached cell S after the stimulation step are performed. Hereinafter, each of the steps will be described in detail.

Figure 3:
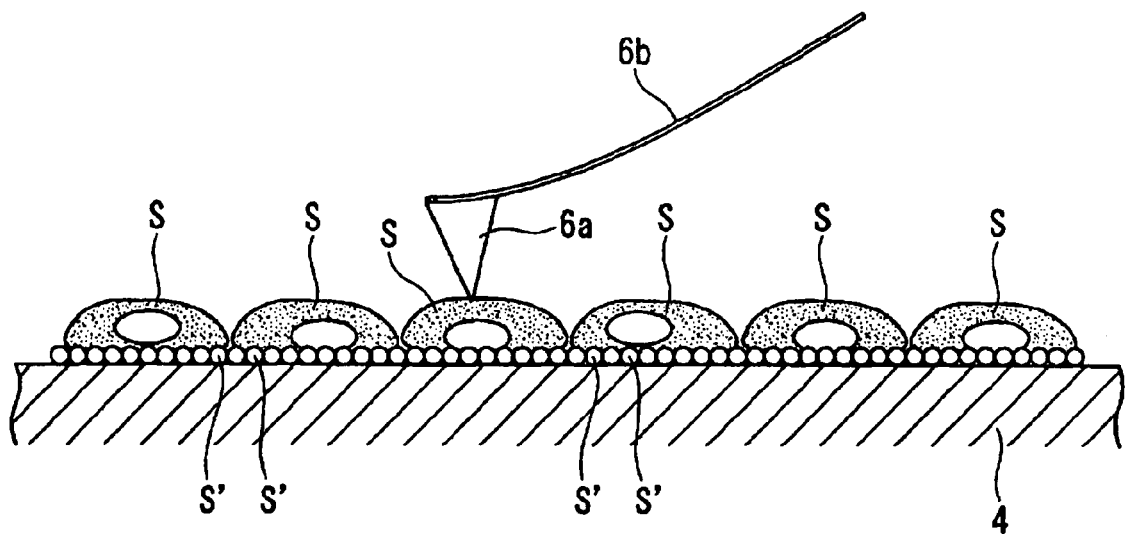
FIG. 3 is a diagram showing a process of a case of performing the cell detachment method according to this invention by using the cell detachment system of FIG. 1, wherein a state of moving a probe onto a specified cell is shown.

The plural cells S are cultured as being spread on the bottom of the cell 4 kept under predetermined culture conditions as shown in FIG. 3. In this state, each of the cells S adheres to the bottom of the cell 4 and the adjacent cells S by a secreted extracellular matrix S'.

Also, as an initial setting for the displacement measurement unit 7, positions of the semiconductor laser light source 15 and the laser light receiving unit 16 are adjusted. More specifically, the position adjustment is performed so as to allow the laser light L emitted from the semiconductor laser light source 15 to enter the reflection surface of the lever 6b as well as to allow the laser light L reflected by the reflection surface to enter the laser light receiving unit 16 without fail. After that, the state in which the semiconductor laser light source 15 is made ready to emit the laser light L and the laser light receiving unit 16 is made ready to detect the laser light L reflected by the reflection surface of the lever 6b is maintained.

After the completion of the above initial setting, the observation step is performed during the culture. More specifically, a culture state of the plural cells S cultured in the cell 4 is observed by using the optical microscope 3 from the direction of the lower surface of the cell 4. The operator judges whether or not there is the cell S to be eliminated, i.e. a mutant cell, a cell with a certain abnormality, or the like, while confirming the observed image on the monitor 17. As a result, in the case where the cell S to be eliminated is found, a position of the cell is specified.

After specifying the position of the cell S, the moving step for moving the probe 6a onto the cell S is performed. More specifically, the probe 6a is positioned on the specified cell S by appropriately moving the XYZ scanner 10 in the XYZ-directions as shown in FIG. 3. Since the moving step is performed by confirming through the monitor 17 the image picked up by the optical microscope 3, it is possible to accurately position the probe 6a on the specified cell S.

Figure 4:
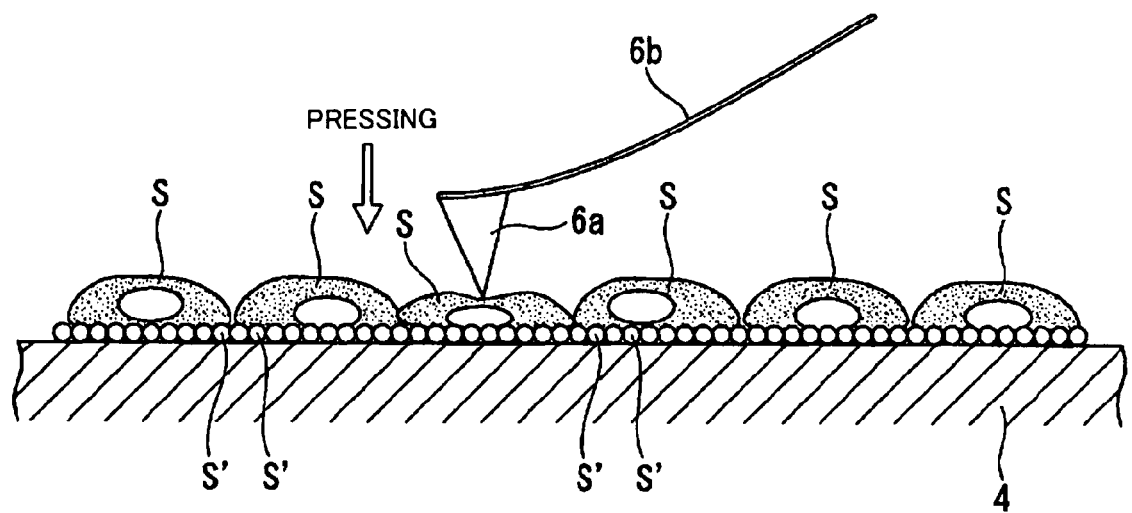
FIG. 4 is a diagram showing a state wherein stimulation is given by pressing the probe to the cell after the state of FIG. 3.

Next, the stimulation step for giving physical stimulation to the specified cell S by pressing the tip of the probe 6a against the cell S with a predetermined force for a certain period of time is performed. More specifically, as shown in FIG. 4, the XYZ scanner 10 is minutely moved in the Z-direction (direction vertical to the substrate or cell bottom) which is the direction in which the probe 6a and the cell S gradually approach to each other. Since the lever 6b starts to deflect with the minute movement, the position of the laser light L entering the light receiving unit 16 (the laser light L reflected by the reflection surface) is changed. The laser light receiving unit 16 outputs to the control unit 8 a deflection signal responsive to the change. The control unit 8 compares the deflection signal and a rated value that has been specified in accordance with the type of the cell S to stop the drive circuit 11 at a time point when the deflection signal reaches to the rated value. With such constitution, it is possible to give stimulation to the cell S without crushing the cell S and in a state where influence to be exerted on the cell S is reduced as much as possible.

Figure 5:
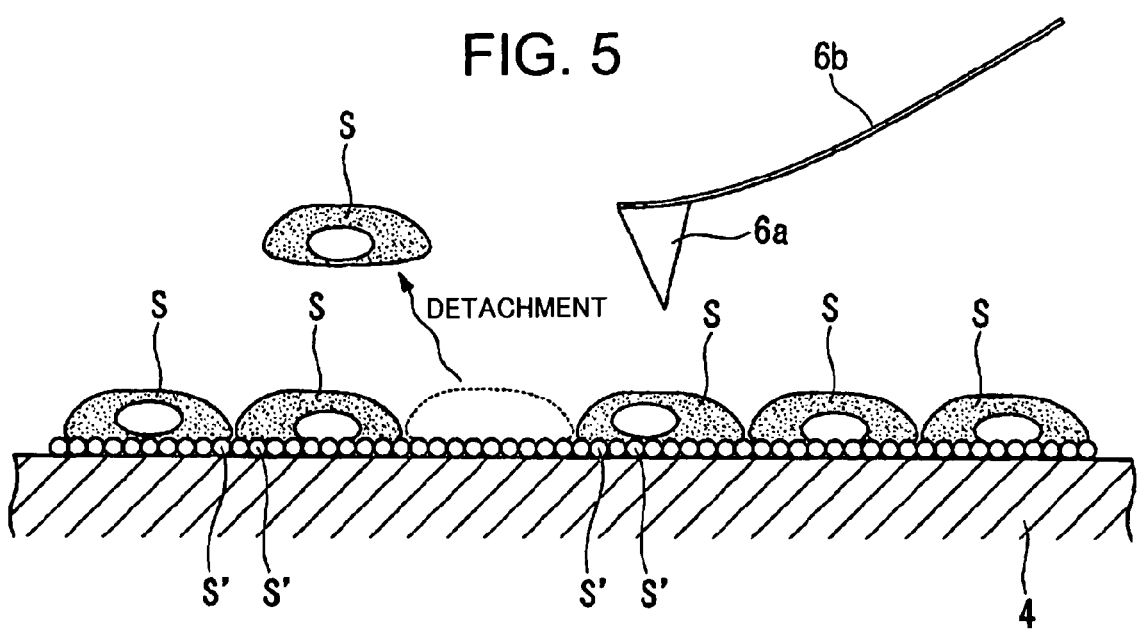
FIG. 5 is a diagram showing a state wherein the stimulated cell is detached from the cell after the state of FIG. 4.

Upon reception of the stimulation, the cell S is brought into a state where activity temporarily ceases or stops and the adhesive force is weakened. Due to the weakened adhesive force exhibited by the cell S, the cell S can no longer adhere to the cell 4 and the adjacent cells S and starts to float in the culture medium W as shown in FIG. 5. As a result, it is possible to remove the cell S specified in the observation step by detaching the cell S from the bottom of the cell 4.

Lastly, the capturing step for capturing (pinching) the cell S floating in the culture medium W by using a cell pinching unit 18 such as a pipette as shown in FIG. 1 is performed.

Particularly, since the stimulation is given only to the specified cell S to detach the cell S from the cell 4 in the cell detachment method of this embodiment, the rest of the cells S are free from any influences and maintain the adhesion state. In other words, as is different from the conventional methods in which the cells are easily damaged and inevitably detached at once, it is possible to detach only the desired cell S from the plural cells S cultured on the cell 4 without exerting influence on the rest of the cells S.

Therefore, it is possible to perform various cultures since it is possible to perform the detachment which had been difficult with the conventional methods. Also, since it is possible to continue to culture the rest of the cells S by using the same cell 4, this method achieves handling easiness.

Also, since this method does not use a special tool such as the cell culture sheet used in the conventional methods, this method is not restricted by the type of cells. Further, since the cell S to be detached is stimulated with the predetermined force that is not more than a force for stopping the activity of the cell S, it is possible to suppress as much as possible the influence to be exerted on the cell S, and the cell S is not crushed. This advantage is also achieved without exerting influence on the rest of the cells S and the culture environment, too.

Also, since the specified cell is captured after the detachment, it is possible to eliminate the sell S from the culture environment. Therefore, it is possible to reliably reduce the influence to be exerted on the rest of the cells S.

In the above-described embodiment, it is preferable to perform the observation step during the culture of the rest of the cells S as required after detaching the specified cell S. With such observation step, in the case where a cell S (ex. mutant cell) unnecessary for the culture appears again in the course of progress of the culture, it is possible to eliminate the cell S again by performing the moving step and the stimulation step. Therefore, even in the case of performing the culture for a long time, it is possible to continue the culture by selecting the necessary cells S.

Also, the force for pressing the probe 6a against the cell S is decided depending on the type of the cell S in advance of the pressing in the above-described embodiment, and the force may be decided depending on at least one of conditions of the type of the cell S, the size of the cell S, and the culture state (culture period, culture temperature, and the like). Thus, it is possible to give stimulation with the influence to be exerted on the cell S being suppressed to minimum. Preferably, the force for pressing the probe 6a against the cell S is less than 100 μN.

Also, in the stimulation step in the above-described embodiment, the stimulation may be given to the specified cell S while scanning a surface of the cell S in the state where the probe 6a is pressed against the cell S.

More specifically, the surface of the cell S is scanned with the probe 6a by appropriately moving the XYZ scanner 10 while pressing the probe 6a against the cell S, not by simply pressing the probe 6a against the cells. By scanning the surface of the cell S, it is possible to give stronger stimulation, thereby making it possible to reliably detach the cell S even when the cell S adheres firmly. Particularly, when the size of the cell S is large, it is possible to detach the cell S more easily since it is possible to give stimulation uniformly to a whole part of the cell S.

Also, in the stimulation step in the above-described embodiment, the stimulation may be given to the specified cell S while vibrating the probe 6a in at least one of the XY-directions and the Z-direction in the state where the probe 6a is pressed against the cell S.

Figure 6:
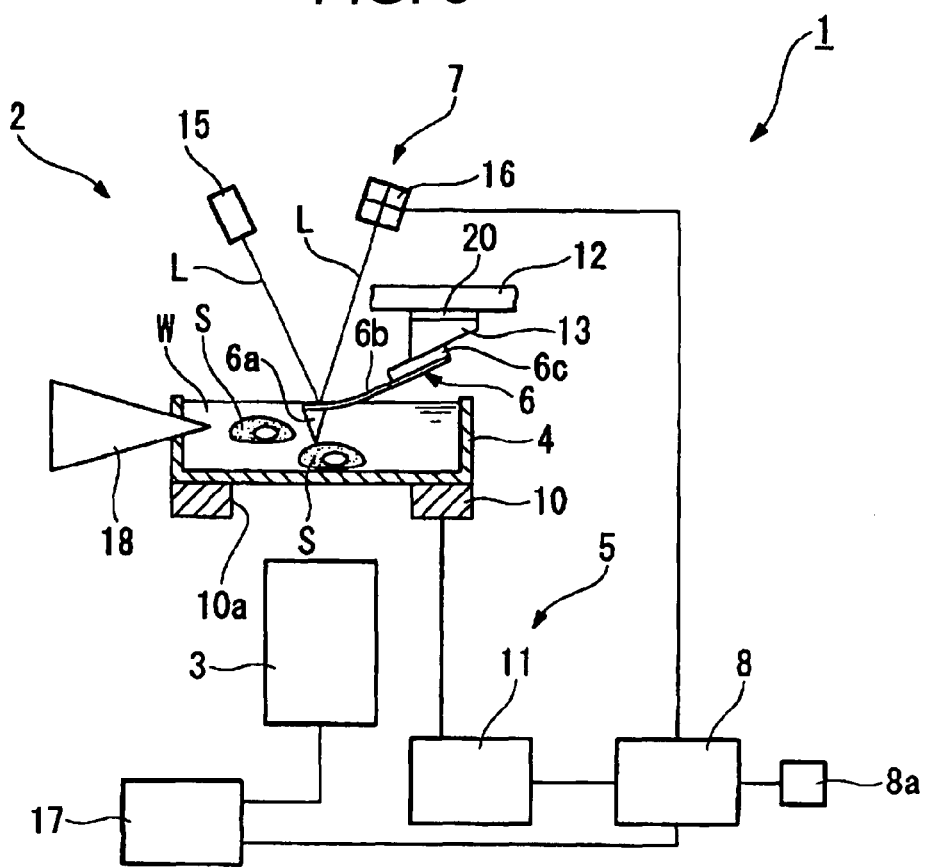
FIG. 6 is a block diagram showing a modification example of the cell detachment system shown in FIG. 1, wherein the cell detachment system has a vibration mechanism for vibrating the probe.

In this case, a vibration mechanism 20 vibrating in a predetermined direction upon application of a voltage is provided between the holder main body 12 and the slope block 13 as shown in FIG. 6.

Figure 7:
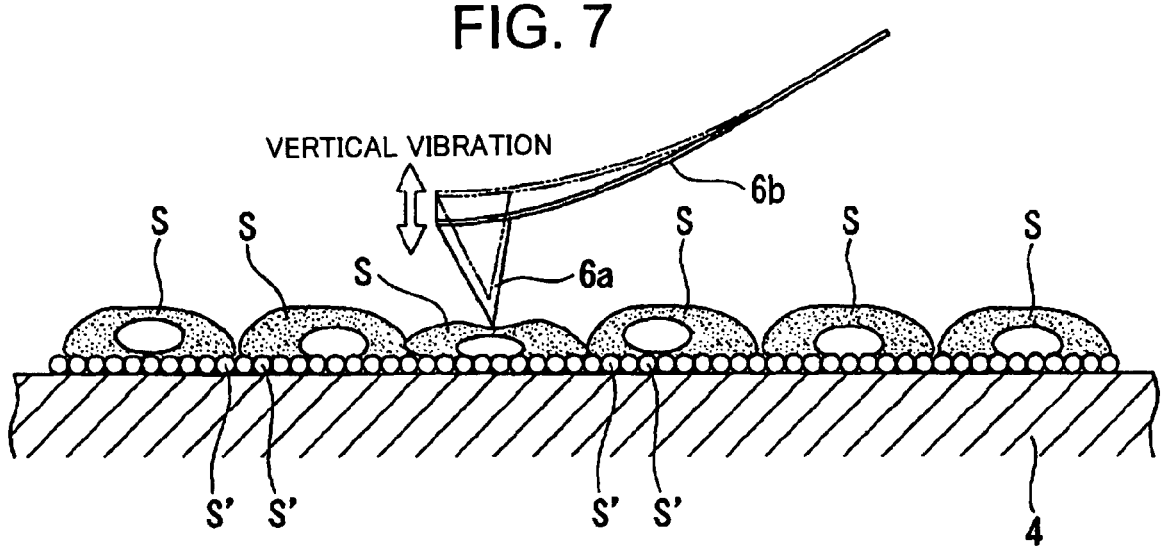
FIG. 7 is a diagram showing a process of a case of performing the cell detachment method according to this invention using the cell detachment system shown in FIG. 6, wherein a state of pressing the probe against the cell while vertically vibrating the probe is shown.
Figure 8:
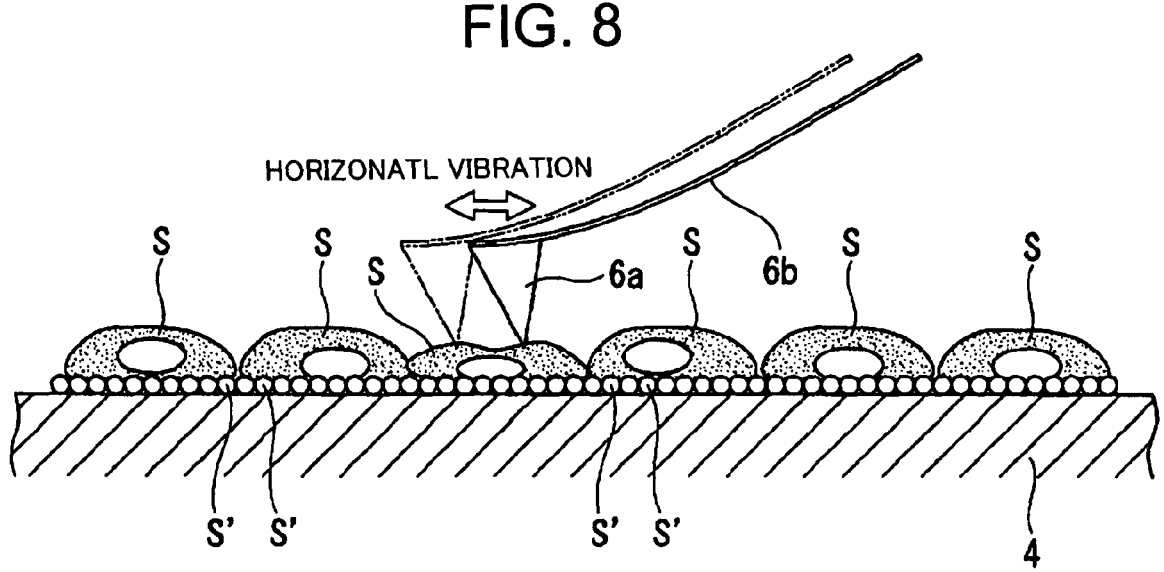
FIG. 8 is a diagram showing a process of a case of performing the cell detachment method according to this invention using the cell detachment system shown in FIG. 6, wherein a state of pressing the probe against the cell while horizontally vibrating the probe is shown.

With the provision of the vibration mechanism 20, it is possible to press the probe 6a while vertically vibrating the probe 6a in the Z-direction as shown in FIG. 7 as well as to press the probe 6a while horizontally vibrating the probe 6a in the XY-directions as shown in FIG. 8. With this configuration, it is possible to give stronger stimulation, thereby making it possible to reliably detach the cell S even when the cell S adheres firmly.

In the case of giving vibration, the vertical vibration and the horizontal vibration may be combined. Further, the vertical and horizontal vibrations may be combined with the above-described scanning for giving stimulation.

Also, though the example of detaching the cell S with which a mutation evolution or a certain abnormality is found during culture is given in the above-described embodiment, the cell S is not limited to such cell S. For example, a normal cell S may be regularly detached in order to conduct thinning of plural cells S. That is, the cell detachment method of this invention is applicable irrespective of the state of the cell S such as normal and abnormal.

Particularly, in the case of detaching the normal cell S, a passage culture step for culturing the captured cell S in another cell kept under predetermined culture conditions may be performed after the capturing step. With the passage culture step, it is possible to use the cell S without wasting the cell S.

Also, it is possible to apply the cell detachment method of this embodiment to elimination of an anaplastic cell by adapting the cell detachment method to the field of regenerative medical techniques.

In recent years, researches have been conducted on differentiation of a parent cell such as an oocyte and an ES cell into a desired tissue cell (such as a hepatocyte or a caridocyte). The differentiation is performed in such a manner that the parent cells are differentiated into the desired tissue cells during a culture, and, in the course of the culture, differentiated cells and cells that are not differentiated (anaplastic cells) appear. In such case, it is necessary to eliminate the anaplastic cells since they are unnecessary for the rest of the culture.

In order to eliminate the anaplastic cells, an operation of detaching the entire cells once in mid-course of the culture and then separating the cells from one another by using a cell sorter to return the differentiated cells has heretofore been conducted. Such operation not only requires the labor and time but also damage the differentiated cells.

In contrast, by employing the cell detachment method of this embodiment, it is possible to specify and detach only the anaplastic cell S from the whole cells S cultured without influencing on the rest of the cells S. Therefore, since it is possible to largely reduce the time and labor as well as to culture the rest of the cells S without damaging them, it is possible to conduct a more accurate research.

In the above-described embodiment, it is possible to perform a co-culture step for culturing a cell S of a different type by placing the different cell at a position of the detached cell S. By performing this step, it is possible to perform the co-culture of plural types of cells S as well as to obtain the desired tissue cell S.

More specifically, after detaching the cell S by the stimulation step, the different cell S is placed at a vacant position on the bottom of the cell 4, i.e. the position to which the detached cell S adhered, by manipulation. The different cell S adheres to the cell 4 by secreting an extracellular matrix S' in the course of time. Thus, it is possible to co-culture at least two types of cells S (such as cells S for forming a vein and cells S for forming a muscle). As described above, it is possible to preferably apply the cell detachment method of this embodiment to the case of performing co-culture.

EXAMPLE

Hereinafter an example of actually performing the detachment of a cell S based on the embodiment will be described with reference to FIGS. 9A to 9D. The detachment of the cell S was performed under the following conditions.

As the cells S, Chinese hamster ovary cells (CHO) were used. In the stimulation step, stimulation was given to one of the cells S by scanning a substantially center of the cell S for three reciprocations while pressing the probe 6a against the cell S and vibrating the probe 6a vertically.

Figure 9A:
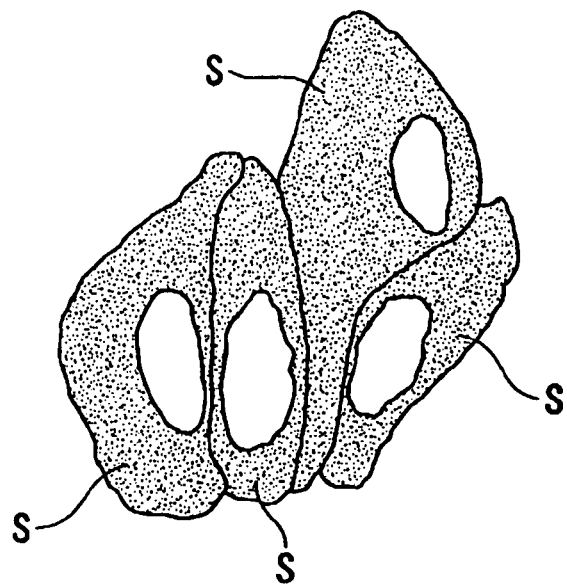
Figure 9B:
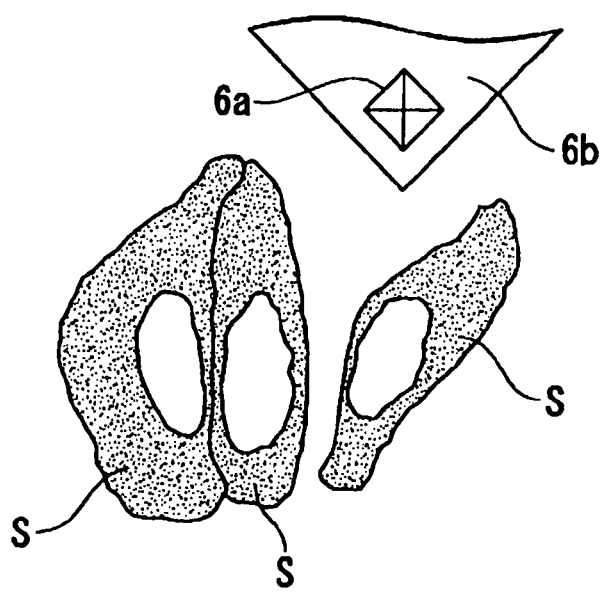
Figure 9C:
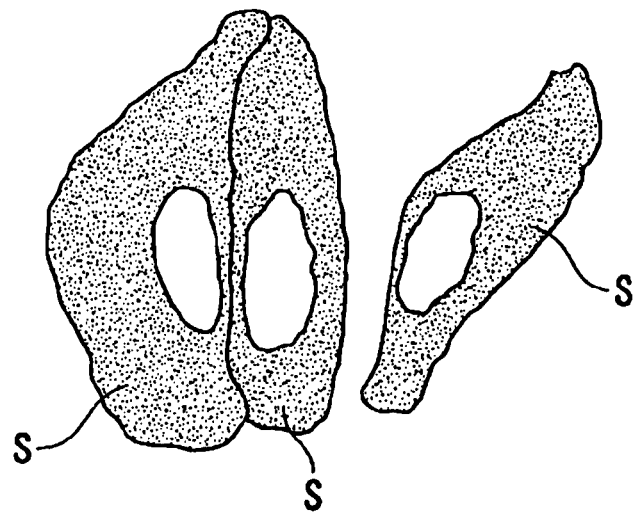
Figure 9D:
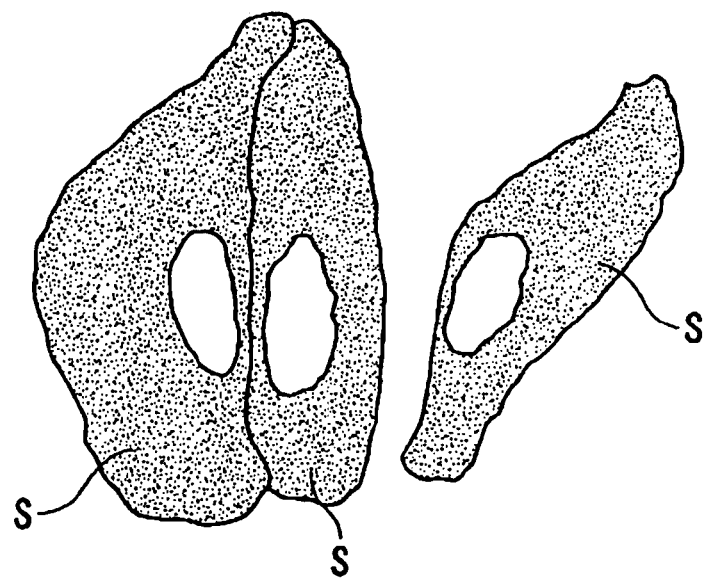
Figure 10:
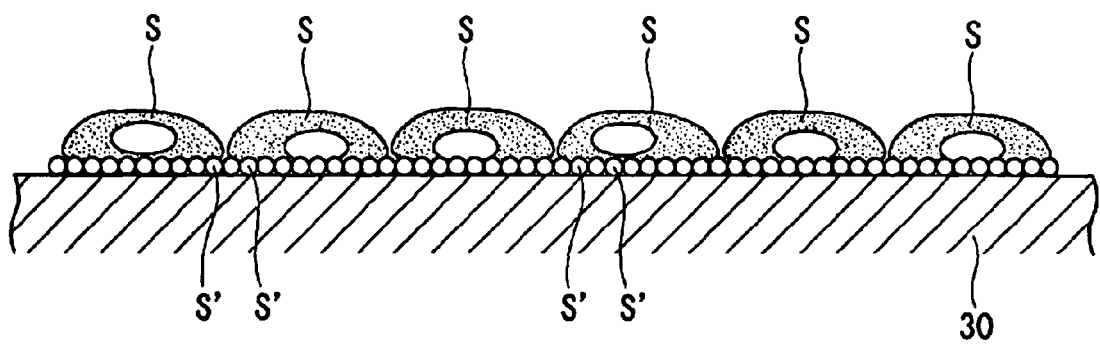
FIG. 10 is a diagram used for explaining a conventional cell detachment method, wherein a state of culturing plural cells on a substrate is shown.
Figure 11:
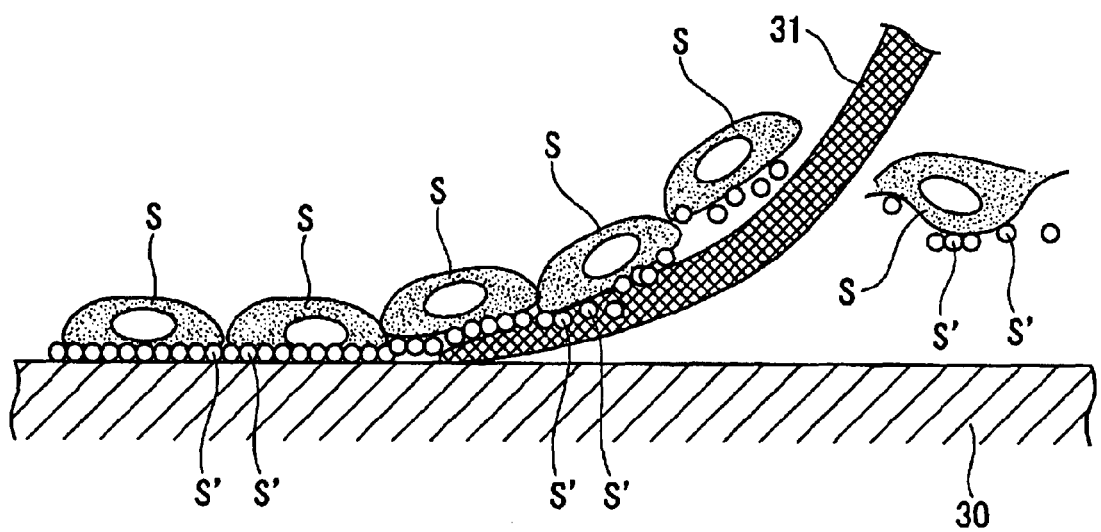
FIG. 11 is a diagram used for explaining a conventional cell detachment method, wherein a state of detaching plural cells by using a scraper is shown.
Figure 12:
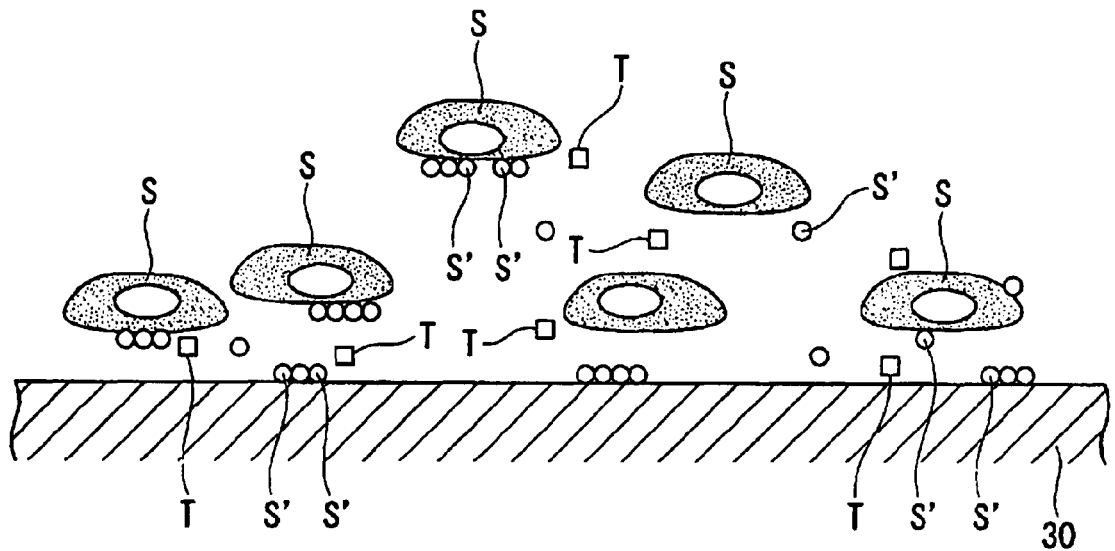
FIG. 12 is a diagram used for explaining a conventional cell detachment method, wherein a state of detaching plural cells by employing a chemical treatment using a reagent is shown.
Figure 13:
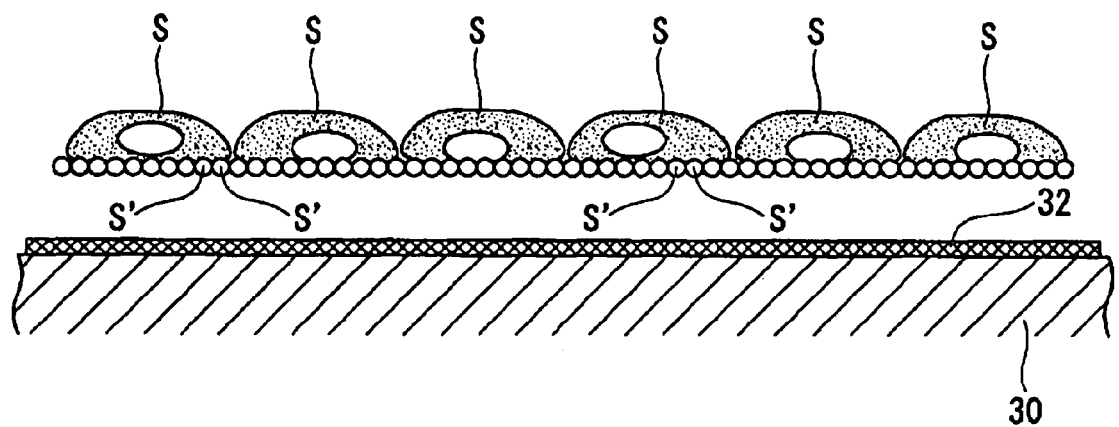
FIG. 13 is a diagram used for explaining a conventional cell detachment method, wherein a state of detaching plural cells by using a cell culture sheet is shown.

Under the above-described conditions, the stimulation was given to the cell S which is the second cell from the right among the four cells S shown in FIG. 9A. As shown in FIG. 9B, the cell S to which the stimulation was given was detached and removed. Also, 10 minutes after the detachment, it was confirmed that the rest of the cells S that were continuously cultured extended as shown in FIG. 9C. Further, 30 minutes after the detachment, it was confirmed that the rest of the cells S further extended as shown in FIG. 9D.

As described above, the advantageous effect of detaching only the desired cell S without exerting any influences on the rest of the cells S, which had not been attained by the conventional techniques, was confirmed.

Note that the scope of this invention is not limited to the above-described embodiment, and it is possible to add various alterations insofar as the alternations do not deviate from the scope of the invention.

For example, though the scanning method in the above-described embodiment was conducted by moving the cell 4 in the three-dimensional directions, the scanning method is not limited thereto, and it is possible to perform a probe scanning method wherein the probe unit 6 is moved in the three-dimensional directions. In this case, though the scanning method is different from the above-described one, the same effects are achieved. Also, a structure wherein both of the cell 4 and the probe unit 6 are moved in the three-dimensional directions may be adopted.

Though the displacement measurement unit 7 measures the deflection of the lever 6b by employing the optical lever method using the laser light, the measurement method is not limited to the optical lever method. For example, a structure wherein the deflection of the lever 6b is measured by an auto-detection method using a displacement detection mechanism (for example, piezoresistance element) provided to the lever 6b itself may be adopted.

Also, though the case of using the optical microscope 3 is described above, any observation unit may be used insofar as the observation unit is capable of confirming a culture state of cells S and positioning of probe 6a. For example, a CCD or the like may be used. The optical microscope 3 is more preferred since it is possible to observe the culture state of cells S by employing a method of fluorescence observation and the like when the optical microscope 3 is used.

The invention claimed is:

1. A cell detachment method for detaching only a desired cell from a plurality of cells cultured on a substrate under predetermined culture environment conditions using a scanning probe microscope having a probe provided at a distal end portion of a deflectable lever, comprising:

an observation step for observing the plural cells and specifying the cell to be detached;

a moving step, performed after the observation step, for moving the probe of the scanning probe microscope in a direction vertical to the substrate to position a tip of the probe on the surface of the specified cell;

a stimulation step, performed after the moving step, for giving physical stimulation to the specified cell by pressing the probe against the specified cell with a predetermined force in order to detach the specified cell from the substrate, the stimulation step comprising gradually pressing the probe in a direction vertical to the substrate against the specified cell with the predetermined force to cause deflection of the lever, detecting a change in deflection of the lever caused by pressing the probe against the specified cell, and stopping the pressing of the probe against the specified cell when the change in deflection of the lever reaches a preset rated value that signifies a temporary cessation of cell activity and weakening of the adhesive force exhibited by the specified cell to cause the specified cell to detach from the substrate; and a capturing step for capturing the detached cell, the capturing step being performed after the stimulation step.

2. The cell detachment method of claim 1; wherein the force for pressing the probe against the specified cell is decided depending on at least one of conditions of a type of the specified cell, a size of the specified cell, and a culture state.

3. The cell detachment method of claim 1; wherein the force for pressing the probe against the specified cell is less than 100 µN.

4. The cell detachment method of claim 1; wherein the observation step, the moving step, and the stimulation step are repeated during a culture of the rest of the cells after detaching the specified cell.

5. The cell detachment method of claim 1; wherein the stimulation is given to the specified cell while scanning a surface of the cell in the state where the probe is pressed against the cell when performing the stimulation step.

6. The cell detachment method of claim 1; wherein the stimulation is given to the specified cell with the probe being vibrated in at least one of a direction vertical to a surface of the substrate and a direction horizontal to the surface of the substrate in the state where the probe is pressed against the cell when performing the stimulation step.

7. The cell detachment method of claim 1; further comprising a co-culture step for co-culturing a cell of a different type by placing the different cell at a position of the detached cell, the co-culture step being performed after the stimulation step.

8. The cell detachment method of claim 1; further comprising a passage culture step for culturing the captured cell on another substrate under predetermined culture environment conditions, the passage culture step being performed after the capturing step.

9. A cell detachment method for detaching only a desired cell from a plurality of cells cultured on a substrate under predetermined culture environment conditions using a scanning probe microscope having a probe provided at a distal end portion of a deflectable lever, comprising:

observing the plural cells;

specifying the cell to be detached;

moving the probe of the scanning probe microscope in a direction vertical to the substrate to position a tip of the probe on the surface of the specified cell;

gradually pressing the probe in a direction vertical to the substrate against the specified cell with a predetermined force to cause deflection of the lever;

detecting a change in deflection of the lever caused by pressing the probe against the specified cell;

stopping the pressing of the probe against the specified cell when the change in deflection of the lever reaches a preset rated value that signifies a temporary cessation of cell activity and weakening of the adhesive force exhibited by the specified cell to cause the specified cell to detach from the substrate; and capturing the detached cell.

10. The cell detachment method of claim 9; wherein the force for pressing the probe against the specified cell is less than 100 µN.

11. The cell detachment method of claim 9; wherein the probe is pressed against the specified cell while scanning a surface of the specified cell.

12. The cell detachment method of claim 9; wherein the probe is pressed against the specified cell with the probe being vibrated in a direction vertical to a surface of the substrate.

13. The cell detachment method of claim 9; wherein the probe is pressed against the specified cell with the probe being vibrated in a direction horizontal to the surface of the substrate.

14. The cell detachment method of claim 9; further comprising co-culturing a cell of a different type by placing the different cell at the position vacated by the detached cell.

15. The cell detachment method of 9; further comprising subculturing the captured cell on another substrate under predetermined culture environment conditions.

16. The cell detachment method of claim 1; wherein, in the stimulation step, the specified cell is detached from the substrate without being physically scraped off the substrate by the probe.

17. The cell detachment method of claim 9; wherein the specified cell is detached from the substrate without being physically scraped off the substrate by the probe.

* * * * *